United States Patent [19]

Weissman et al.

[11] Patent Number: 4,738,928

[45] Date of Patent: Apr. 19, 1988

[54] METHOD FOR CLONING GENES

[75] Inventors: Sherman M. Weissman, New Haven, Conn.; Dennis Pereira, Westerly, R.I.; Ashwani Sood, New Haven, Conn.

[73] Assignee: Yale University, New Haven, Conn.

[21] Appl. No.: 846,481

[22] Filed: Mar. 31, 1986

Related U.S. Application Data

[60] Continuation of Ser. No. 513,524, Jul. 13, 1983, abandoned, which is a division of Ser. No. 217,643, Dec. 18, 1980, Pat. No. 4,394,443.

[51] Int. Cl.$^4$ .................. C12N 1/20; C12N 15/00; C12N 5/00; C12N 1/00; C12P 21/00; C12P 21/02; C12P 2/104; C12P 19/34; C07H 21/04

[52] U.S. Cl. .................. 435/253; 435/68; 435/70; 435/71; 435/91; 435/172.1; 435/172.3; 435/240.2; 435/243; 435/240.1; 435/317.1; 435/320; 536/27; 935/9; 935/12; 935/29; 935/72; 935/73

[58] Field of Search ............ 435/68, 70, 91, 172.3, 435/71, 317, 253, 243, 172.1, 317.1, 240.1, 240.2, 240.23, 240.25, 240.26, 240.4, 240.45, 240.46, 240.47; 536/27; 935/9, 12, 29, 72, 73

[56] References Cited

U.S. PATENT DOCUMENTS 4,293,652 10/1981 Cohen .................. 435/91

OTHER PUBLICATIONS

Sanger, et al., "DNA Sequencing with Chain-Terminating Inhibitors", Proc. Natl. Acad. Sci. U.S.A 74: 5463 (1977).

Houghton, et al., "The Amino-Terminal Sequence of Human Fibroblast Interferon as Deduced from Reverse Transcripts Obtained Using Synthetic Oligonucleotide Primers", Nucl. Acids. Res. 8: 1913 (1980).

Itakura, et al., "Expression in *Escherichia coli* of a Chemically Synthesized Gene for the Hormone Somatostatin", Science 198: 1056 (1977).

Ploegh, et al., "Molecular Cloning of a Human Histocompatibility Antigen cDNA Fragment", Proc. Natl. Acad. Sci. U.S.A 77: 6081 (1980).

Orr, et al., "Comparison of Amino Acid Sequence of Two Human Histocompatibility Antigens, HLA-A2 and HLA-B7: Location of Putative Alloantigenic Sites", Proc. Natl. Acad. Sci. U.S.A 76: 4395 (1979).

Noyes, et al., "Detection and Partial Sequence Analysis of Gastrin mRNA by Using an Oligodeoxynucleotide Probe", Proc. Natl. Acad. Sci. U.S.A 76: 1770 (1979).

*Primary Examiner*—James Martinell
*Attorney, Agent, or Firm*—Millen & White

[57] ABSTRACT

A method is provided for isolating and identifying a recombinant clone having a DNA segment therein coding for at least one desired heterologous polypeptide, at least a short amino acid sequence of which is known, by effecting cDNA synthesis on a mixture of mRNAs containing the mRNA coding of the desired polypeptide, isolating the resultant cDNA mixture, inserting the resultant cDNA into recombinant cloning vehicles, transforming hosts with the vehicles, separating the transformants and isolating and identifying a recombinant clone containing a DNA segment which is homologous over at least a portion thereof to at least one oligonucleotide probe specific for the DNA segment; wherein the probe is an extension of the nucleotide sequence of an oligonucleotide primer having a nucleotide sequence complementary to a region of the target mRNA coding for a portion of the known amino acid sequence, and is complementary to a longer region of the target mRNA coding for a longer portion of the known amino acid sequence. Recombinant clones coding for human histocompatibility antigens are provided, in particular, clones for HLA-B antigens.

18 Claims, No Drawings

METHOD FOR CLONING GENES partial support for this invention was provided by the National Institutes of Health and/or The American Cancer Society.

This application is a continuation of application Ser No. 513,524, now abandoned, filed July 13, 1983, which is a divisional application of Ser. No. 217,643 of 12/18/80, U.S. Pat. No. 4,394,443.

BACKGROUND OF THE INVENTION

The present invention relates to a method for isolating and identifying a recombinant clone having a DNA segment therein coding for a polypeptide at least a short amino acid sequence of which is known. The present method is illustrated by its application to the production of clones containing a plasmid incorporating DNA coding for human histocompatibility antigens of the HLA-B region.

Recombinant DNA techniques are now quite well known. See, e.g., Morrow, "Recombinant DNA Techniques" in *Methods In Enzymology*, 68, 3-24 (Academic Press, 1979), and references cited therein, all of which are incorporated herein by reference. See also UK patent application Nos. GB2,007,675A, 2,007,676A and 2,008,123A, the disclosures of which are also incorporated herein by reference. Genes coding for various polypeptides may be cloned by incorporating a DNA fragment coding for the polypeptide in a recombinant DNA vehicle, e.g., a bacterial or viral plasmid, and transforming a suitable host, typically an *Escherichia coli* (*E. coli*) cell line, and isolating clones incorporating the recombinant plasmids. Such clones may be grown and used to produce the desired polypeptide on a large scale.

DNA for cloning may be obtained in at least three ways. DNA extracted from cellular material may be used, either as such or after excision of various portions. Alternatively, DNA can be synthesized chemically, provided the nucleotide sequence is known or the amino acid sequence of the desired polypeptide is known.

A third method of producing DNA for cloning is reverse transcriptase catalyzed synthesis in the presence of mRNA. However, known techniques for isolating and identifying cDNA produced from RNA by reverse transcription are inadequate for cloning cDNAs for which the corresponding mRNA constitutes a very minor proportion of the total mRNA from a cell type.

The use of oligonucleotide primers to detect yeast cytochrome C mRNA and gastrin mRNA has been reported (Szostak et al, *Nature*, 265, 63 (1977); Noyes et al, *Proc. Natl. Acad. Sci. USA*, 76, 1770 (1979)). The use of dideoxynucleoside triphosphates (ddNTPs) and arabinosyl triphosphates for sequencing DNA (Sanger, et al., *Proc. Natl. Acad. Sci. USA*, 74, 5463 (1977)) and for sequencing RNA (Zimmeren et al, *Proc. Natl. Acad. Sci. USA*, 75, 4257 (1978)) is known.

The histocompatibility region (HLA) in humans is a complex gene family located on chromosome 6. The genes in this region are related to immune responses, and tend to be highly polymorphic, reflecting the highly individual immune response of humans. The best studied and most relevant loci within the HLA region are the HLA-A, HLA-B, HLA-C, HLA-D and HLA-DRW loci. See Perkins, "The Human Major Histocompatibility Complex (MHC)", in *Basic And Clinical Immunology, 2d Edition*, 165-174 (Lange Medical Publ., 1978) for further details regarding this complex.

Antigens coded for by the HLA loci are primarily proteins located on the cell's exterior surface, and allow the cells to recognize self from non-self. At a cellular level, these antigens are involved in the recognition of host from foreign cells, and enable a population of lymphocytes called helpers T cells to be activated and participate in the activation of macrophage, B cells and killer T cells. In attempts to graft tissue from a different donor, a mismatch of any of these HLA loci results in a graft/host reaction which ultimately can lead to the rejection of mismatched organs by patients.

The proteins coded for by the HL region comprise only about 0.05 to 0.1% of the total cellular proteins and @about 1% of the membrane associated protein of lymphoblastoid cell lines. The antigens of the HLA-A, HLA-B and HLA-C regions tend to co-purify and are therefore difficult to isolate. In addition, isolation of these antigens from human cell lines would be expensive. Consequently, the separation of individual genes and production of specific antigens by conventional procedures is fraught with difficulty.

Other genes of biological interest are also difficult to isolate, for many of the reasons that hold for HLA antigens. Even where full or partial amino acid sequences are available for the corresponding proteins, a low proportion of mRNA corresponding to the gene still makes isolation and characterization difficult.

A reed therefore continues to exist for a method for cloning genes for polypeptides whose corresponding mRNA is a minor fraction of the total mRNA in an mRNA mixture, especially a method sensitive to mRNA present in the mixture below the level of 2 mole %, eg., up to about 1 mole % on up to about 0.1 mole %, and even below 0.01 mol %.

OBJECTS OF THE INVENTION

One object of the present invention is to provide a method for cloning genes, where the mRNA corresponding to the gene is a very minor constituent of an mRNA mixture.

Another object of the invention is to provide a means of producing desired polypeptides by expression of genes coding for these polypeptides in clones of transformed plasmid hosts containing recombinant plasmids incorporating DNA segments for the genes.

A further object of the invention is to provide DNA segments, plasmids incorporating the segments and transformed hosts containing the plasmids, where the DNA segments code for desired polypeptides.

Yet another object of the invention is to provide clones containing genes for histocompatibility antigens.

Upon further study of the specification and appended claims, further objects and advantages of this invention will become apparent to those skilled in the art.

SUMMARY OF THE INVENTION

Briefly, these objects and others which will hereinafter become apparent may be achieved by a method for isolating and identifying a recombinant clone having a DNA segment therein coding for at least one desired heterologous polypeptide, at least a short amino acid sequence of which is known, said method comprising the steps of:

(a) effecting cDNA synthesis on a mixture of mRNAs containing a target mRNA coding for said at least one polypeptide, and isolating the resultant cDNA mixture;

(b) inserting said resultant cDNA into recombinant cloning vehicles, and transforming hosts with said vehicles; and (c) separating the transformants and isolating and identifying a recombinant clone containing a DNA segment which is homologous over at least a portion thereof to at least one oligonucleotide probe specific for said DNA segment; wherein said probe is a extension of the nucleotide sequence of an oligonucleotide primer having a nucleotide sequence complementary to a region of said target mRNA coding for a portion of said known amino acid sequence, and is complementary to a longer region of said target mRNA coding for a longer portion of said known amino acid sequence.

DETAILED DISCUSSION

A useful method for cloning genes coding for a desired polypeptide involves inserting a cDNA segment into a vehicle, transforming a host and isolating recombinant clones. Where the mRNA coding for the polypeptide is a minor constituent of a diverse mRNA mixture, isolation and identification of the corresponding cDNA is extremely difficult. Reverse transcription typically is effected using a nonspecific primer, e.g., oligo(dT)$_{12-18}$, which results in extension from virtually all mRNAs. Those cDNA species from mRNA constituents present to the extent of at least about 2 mole % of the total mRNA will be seen distinctly above the background, while cDNA from minor constituents will not. Until now, isolation and identification of such minor cDNA products would have required analysis of all cDNA produced, a formidable task which had rendered this method practically unworkable.

The present invention provides a general method for solving this problem. Not only is sensitivity increased by several orders of magnitude, but the present method permits cloning genes for polypeptides for which neither complete amino acid sequences nor complete DNA or mRNA sequences are known. It is not even necessary for the polypeptide to be pure, so long as a major fragment can be isolated.

The sole requirement is knowledge of a short amino acid sequence, e.g., 5–25, preferably at least 15, amino acid residues, in the polypeptide of interest. An oligonucleotide primer is synthesized which is predicted to be complementary to a region of the mRNA coding for a portion of the known amino acid sequence. The primer is used to prime reverse transcription on a mixture of mRNAs containing the target mRNA. The use of a specific oligonucleotide primer gives rise to a relativly small number of cDNA products depending on the length of the oligonucleotide. At least a ten-base sequence is preferred, with an undecanucleotide or a dodecanucleotide being particularly preferred. Unless the known amino acid sequence has a 4 or 5 peptide sequence coded for by unique mRNA codons, use of a primer having more than about 14–16 nucleotides is counterproductive, since there is a higher probability of a mismatch due to code degeneracy in a longer primer sequence.

The mixture of extended primer cDNAs is typically still quite complex. According to the present method, a further reduction in complexity is achieved by the use of various techniques for limiting the length of primer chain extension products.

Reverse transcription on the primer may be terminated when a specific nucleotide is required to pair with the mRNA by, e.g., using only three deoxynucleoside triphosphates (dNTPs), or by replacing one of the four dNTPs with the corresponding dideoxynucleoside triphosphate (ddNTP) or an equivalent variant have a base but lacking the proper 3'-OH group. The ddNTP or other variant will be incorporated in the extended primer as the terminal nucleotide.

The extended primer cDNAs are separated and the longer primer extension products are sequenced. The sequence are analyzed to find those that are complementary to a mRNA sequence coding for an extension of the known amino acid sequence used to design the primer. These longer oligonucleotides are used as probes for homologous full length cDNA.

The use of ddNTPs is especially useful to produce oligonucleotide probes. Synthesis of cDNA is effected using an oligonucleotide primer and the same mRNA mixture used initially, with one of the four dNTPs replaced by the corresponding ddNTP. The ddNTPs comprise dideoxyadenosine triphosphate (ddATP), dideoxycytidine triphosphate (ddCTP), dideoxyguanosine triphosphate (ddGTP) and dideoxythymidine triphosphate (ddTTP). One of these ddNTPs and the three dNTPs containing the other three bases are supplied to the mRNA mixture together with the oligonucleotide primer and reverse transcriptase. The reaction is advantageously repeated three more times, using a different ddNTP each time. Each run will produce a cDNA mixture containing the ddNTP as its terminal nucleotide.

The resultant cDNA mixture from each run is separately fractionated, e.g., by gel electrophoresis, and those individual cDNA bands corresponding to oligonucleotides having at least four more nucleotides than the oligonucleotide primer are sequenced and compared to the known partial amino acid sequence of the desired polypeptide. Chain-terminated probes are selected whose nucleotide sequences are complementary to an mRNA sequence coding for an extended amino acid sequence of the known fragment of the desired polypeptide.

It is advantageous to design a primer complementary to an mRNA region coding for amino acids in the polypeptide which are specified by unique codons. To the extent that code degeneracy is avoided, the primer is predicted to be that much more likely to be complementary to the actual mRNA sequence for the particular amino acid sequence used as the predictive model. Where there is degeneracy in the third nucleotide of a codon, its complementary base in the primer should be one which can form a wobble base pair with a mismatched mRNA base. Thus, for example, where the third nucleotide of a codon can be either A or G, the degenerate position in the complementary oligonucleotide primer will be occupied by T rather than C, since T can form a wobble base pair with G as well as a normal base pair with A, while C cannot easily form a wobble base pair with A. In addition, known preferences for and against certain nucleotide sequences in the species whose mRNA is being copied are used to further refine the selection of an appropriate oligonucleotide primer sequence.

Where cDNA synthesis is effected on the mRNA mixture in the presence of the oligonucleotide primer but with only three of the four dNTPs, primer extension will proceed until the messenger RNA code contains the complement of the missing dNTP and will stop at that point. Candidates for oligonucleotide probes will be selected from the primer extension products having at least three more nucleotides than the primer. Again, these will be sequenced and those oligonucleotides complementary to a mRNA sequence coding for a longer portion of the known amino acid sequence of the polypeptide will be identified, isolated and used as probes to recognize full-length cDNA having a homologous sequence.

It will be recognized that variants of these procedures may be used, where they achieve an equivalent result. For example, the use of one purine or pyrimidine deoxyarabinosyl triphosphate in place of the corresponding purine o pyrimidine deoxyribosyl triphosphate will be equivalent to the use of the corresponding ddNTP. Of course, purine or pyrimidine dideoxyarabinosyl triphosphates may also be used in place of purine or pyrimidine dideoxyribosyl triphosphates analogously to the above procedure. In each case, it is advantageous to use four different runs, each with a different dNTP either omitted or replaced by a variant which will result in chain termination at that point. This further reduces the heterogeneity and complexity of the cDNA mixtures and greatly increases the sensitivity of the method.

A further technique for producing longer oligonucleotide probes is to carry out cDNA synthesis on the mRNA mixture in the presence of labeled primer, and then cleave the extended primer cDNAs with an appropriate endonuclease. This gives longer cDNA extension products and may be used in conjunction with chain terminated cDNA synthesis to resolve even more complex mixtures of full-length cDNA products. Any endonuclease capable of cleaving single-stranded DNA can be used, e.g., *aegyptus* III, used previously for sequence analysis of SV 40 mRNA, by Reddy et al, *J. Virol*, 30, 279–296 (1979). Cleavage products of appropriate chain length, e.g., 25–400 nucleotides, preferably 100–350 nucleotides, and optimally about 200 nucleotides, which retain the labeled primer chain, are isolated and sequenced, and probes are identified as before.

The principle of the present method is the same in all cases. First, full-length cDNA synthesis is effected on an mRNA mixture. Then, a short oligonucleotide primer sequence is synthesized which is predicted, on the basis of a known amino acid sequence in the desired polypeptide, to be complementary to a target mRNA coding for that polypeptide. Then, cDNA synthesis is effected on the same mRNA mixture in the presence of the primer, and optionally using means to limit chain extension. Primer extension products are separated and sequenced to find oligonucleotide probes whose nucleotide sequence is complementary to a longer region of the mRNA coding for an extended amino acid sequence corresponding to the known sequence of the desired polypeptide. The full-length cDNA is inserted in a recombinant cloning vehicle which is then used to transform appropriate hosts, and the clones are separated and analyzed. The probe is used to identify clones containing DNA which is homologous in at least one region with the probe sequence.

Homology between clones and probes is determined, in general, by hybridization of DNA isolated from the clones with labeled probe. The activity of the probe can be further increased by effecting cDNA synthesis in the presence of the primer using labeled dNTPs, especially where a probe has already been identified and may be obtained from a specific ddNTP channel.

A further extension of the method, which can lead to higher sensitivity and efficiency, involves the use of a previously identified probe as a new primer for subsequent probe synthesis. This will be most useful where the full-length cDNA mixtures are highly complex, or where only short amino acid sequences of the desired polypeptide are known, separated by substantial unknown regions. In this case, it may be necessary to isolate and sequence several probes differing somewhat in their intermediate nucleotide sequences before a sequence corresponding to another known sequence in the polypeptide is reached and the correct probe is identified. Further variants of the method of the invention will also be apparent, all of which are merely permutations of the aforementioned basic principle, and therefore included within the scope of this invention.

Insertion of the cDNA from full-length reverse transcription into a recombinant cloning vehicle, e.g., a bacterial or viral plasmid, may be effected by any of the various techniques well known in the art. Many plasmids are disclosed in Morrow, "Recombinant DNA Techniques", in *Methods In Enzymology*, 68, at pages 5–15 (1979), and references cited therein. Preferably, vectors existing at high copy numbers and replicating in a relaxed mode are used, since this increases the yield of expressed protein. The plasmid pBR322 is frequently used as a recombinant cloning vehicle. It contains six different types of restriction cleavage termini, and its nucleotide sequence has been determined by Sutcliffe, *Nucleic Acid Res.*, 5, 2721 (1978) (this reference and the references cited therein are incorporated herein by reference).

Plasmids possessing the region of lambda recognized by lambda gene E are called cosmids, and introduction of cloned DNA segments into such vectors has the advantage that the vectors containing the DNA insert can then be packaged in vitro into lambda phage particles. The phage infect and transform bacterial host such as *E. coli* in very high efficiency and yield a very high number of recombinant clones.

In practice, certain recombinant cloning vehicles are more useful than others, and the particular vehicle employed will be chosen as a function of various known factors including, in certain cases, guidelines governing recombinant DNA processes.

The cDNA resulting from reverse transcription is inserted into the cloning vehicles by any one of many known techniques, depending at least in part on the particular vehicle being used. The various insertion methods are discussed in considerable detail in the aforementioned Morrow reference at pages 16–18, and the references cited therein. In general, the vehicle is cleaved by at least one restriction endonuclease, which will either produce a blunt end or a cohesive end. Cohesive ends can be added to blunt-ended vehicles and/or to the DNA to be introduced. The DNA is combined with the vehicle and ligated, if necessary, with an appropriate ligase. Advantageously, the vehicle is treated with, e.g., nuclease-free alkaline phosphatase, to prevent self-sealing.

Once the DNA insert is added, the cloning vehicle is used to transform a suitable host. Such host are generally bacterial strains, e.g., *E. coli* K12 mutants such as *E. coli* HB101, *E. coli* RR1, and the like. The cell line LE392 constructed by Enquist is advantageously used as a host for lambda phage, as reported by Tiemeier et al., *Nature*, 263, 526 (1976).

In general, a host strain must be compatible for the selection procedure used in selecting the clones and must be unable to restrict DNA of "foreign" methylate. That is, when vehicles are used whose selection characteristics rely on antibiotic resistance, the host must not already possess an intrinsic antibiotic resistance to this drug. In addition, the plasmid should be able to replicate in the same host.

For example, a suitable host for the bacterial plasmid pBR 322 must be Ampicillin-sensitive and/or Tetracyclinesensitive, must be free of plasmids of the ColE1 incompatibility group, and must possess the necessary replication mechanism, for example, must be polA+. With regard to resistance to foreign methylate, the restriction-modification system of $E. coli$ K-12 is formed by three genes, hsdR, hsdM and hsdS. The hsdR gene is thought to encode the restriction endonuclease of the K-12 system. The hsdM gene encodes for a peptide which specifically methylates DNA synthesized in the bacteria, which allows for the detection at the DNA level of self from nonself. The hsdS gene is thought to be a locus which provides the substrate (DNA) binding activity of a multimeric restriction-modification enzyme complex. Cells of hsdM$^-$ genotype are unable to modify DNA, those of hsdR$^-$ genotype are unable to restrict foreign DNA and those of hsdS$^-$ genotype are unable either to restrict or to modify DNA. Because the recombinant DNA plasmids seldom posscss the K-12 modification pattern, either because they are synthesized in vitro or because they are isolated from non-K-12 origin, a host must generally either be hsdR$^-$ or hsdS$^-$. (See; *Recomb DNA Res.*, 5, 22 (1980), *Recomb. DNA Tech. Bull.*, 2(3), 128 (1979), *Recomb. DNA Tech. Bull.*, 1(2), 7 (1978))

Once the transformed host containing the DNA segment coding for the desired polypeptide has been isolated and identified, the colony may be further cultured to obtain large quantities of the clone. The recombinant clone will often have extra DNA sequences in the DNA segment coding for the desired polypeptide. These sometimes derive from portions of the cloning vehicle DNA and sometimes result from additions to the insert made for the purpose of facilitating insertion into the vehicle. These extra sequences can be eliminated by judicious digestion with the proper endonucleases. The precise endonucleases will be readily ascertainable once the nucleotide sequence of the areas to be removed has been determined.

In general, the inserted DNA will be trimmed to yield the coding sequence with its terminator intact, and the amino terminal coding sequence as devoid as possible of unnecessary DNA. The essential DNA will be inserted in reading phase with a constitutive or readily inducible regulon, including a ribosomal binding site, a promotor, and an initiator codon. Advantageously, a further coding sequence is included between the promotor and the initiator codon which codes for a signal peptide sequence which would be attached to the desired polypeptide and which would facilitate transport of the hybrid preprotein to the periplasmic space, where it will be cleaved to form the desired polypeptide. The clone may be further amplified by, e.g., chloramphenicol treatment, which can induce a relaxed response which favors plasmid replication over other polynucleotide synthetic processes.

The desired polypeptide may be isolated by, e.g., subjecting the host to a cold osmotic shock procedure, which releases the content of the periplasmic space to the medium. Another alternative or complementary procedure involves the use of certain mutant strains as host, such strains having highly permeable outer membranes which permit periplasmic proteins to diffuse into the medium. These methods of expressing the recombinant DNA are well known to the art, and discussed in considerable detail in the aforementioned references.

The method of the invention may be illustrated by a preferred application to the isolation and identification of recombinant clones containing DNA coding for the production of human histocompatibility antigens (HLAs), particularly HLA-B antigens. The antigens coded for by at least the HLA-A, HLA-B and HLA-C loci are similar in molecular weight and tend to co-purify. It has now been found that an individual HLA mRNA constitutes about 0.01 to 0.05% of poly(A) mRNA in a cellular extract from a lymphoblastoid cell line, in rough agreement with data regarding the percentage of total cellular protein represented by the corresponding antigen.

The general procedure is to culture cells producing HLA antigens, e.g., granulocytes, lymphocytes, and the like, and to extract the RNA by a process such as that disclosed by Ghosh et al, *J. Biol Chem.*, 253, 3643 (1978). Advantageously, the mRNA is enriched for poly(A) mRNA by, e.g., chromatography on oligo(dT) cellulose, followed by elution of the poly(A) mRNA-enriched fraction. This fraction contains as many as 10,000–30,000 different mRNA species.

One of the HLA antigens, HLA-A2, is known to have the tetrapeptide sequence Met-Trp-Arg-Arg. This sequence is advantageous because both methionine and tryptophan have unique codons. The code for arginine has a high degeneracy, since it can be coded for by any of the codons CGN and AGPu (N represents any of the 4 nucleotides and Pu represents a purine nucleotide, either A or G). However, it is known that the dinucleotide CG has a low occurrence in most, although not all, animal cell mRNA. Accordingly, AGPu is a more likely codon, and T is selected for the degenerate position in the complementary oligonucleotide primer. Since, as noted above, T can form a wobble base pair with G.

The undecanucleotide primer $^{3'}$ TAC ACC TCT TC$^{5'}$ is sythesized, e.g., by the triester method (Sood et al, *Nucl. Acid Res.*, 4, 2757 (1977); Hirose et al, *Tet. Lett.*, 28, 2449 (1978)) or other known method of synthesizing oligonucleotides. The primer is then phosphorylated at the 5' end and pre-hybridized with the mRNA mixture. Chain-terminated cDNA synthesis is effected using the primer/mRNA mixture in four separate runs, each run using a different ddNTP as a chain terminator and the three other dNPT's, as well as a reverse transcriptase.

The cDNA from each separate run is soparated, e.g., by electrophoresis, preferably on acrylamide-urea gels, and bands containing cDNA products which are four or more nucleotides longer than the primer are isolated and sequenced. It is known that the amino acid preceding those used for deducing the primer sequence is valine, with a GUN codon in the mRNA. Thus, the cDNA products arising from primer hybridization to HLA mRNA and extension therefrom will contain no more than 13 and 14 nucleotides, respectively, in the ddATP and ddCTP terminated runs. These need not be sequenced. Accordingly, the cDNA products from the ddGTP and ddTTP terminated reactions are analyzed.

A further amino acid sequence is now known for the HLA-B7 antigen, and has the sequence -gly-ala-val-valala-ala-val-met up to the methionine. An mRNA sequence coding for this amino acid sequence is 5'GCN GUN GUN GCN GCN GUN3'. The corresponding complementary probe sequence is 3'CCN CGN CAN CAN CGN CGN CAN (TAC ACC TCT TC)5', with the primer sequence in parenthesis. It can be seen that a cDNA from the ddGTP run might have a ddG in the degenerate 15th position or in the 16th position. Similarly, in the ddTTP run, a probe might be available with a ddT in one of the degenerate positions, i.e., 15, 18, 21, 24, 27 and/or 30. Sequencing of these bands results in isolation of a cDNA product in the 30-nucleotide band of the ddTTP run and one of the cDNAs in the bands at the 16-nucleotide position in the ddGTP run containing sequences complementary to the inferred mRNA sequence corresponding to the known amino acid sequence of HLA-B7. The nucleotide sequence of the 16-nucleotide probe is 5'CTTCTCCACATCACAG3', and the nucleotide sequence of the 30-nucleotide probe is 5'CTTCTCCACATCACAGCAGCGAC-CACAGCT3'.

Although the nucleotide sequence of the primer is predicted to be complementary to the nucleotide sequence in HLA-A2 mRNA, the nucleotide sequence of the 30-nucleotide probe is complementary to a region coding for a known sequence in HLA-B7 antigen. The amino acid sequence of HLA-A2 antigen in this region is unknown, but it is likely to be identical to that of HLA-B7 antigen in this region, since HLA-A2 and HLA-B7 antigens are highly homologous in their amino acid sequences (Orr et al, Proc. Natl. Acad. Sci. USA, 76, 4395 (1979)).

A poly(A)mRNA mixture is reverse transcribed using oligo(dT) primer to form cDNA. The second strand of the cDNA is synthesized with a DNA polymerase, followed by digestion with S1 nuclease to remove the hairpin structure resulting from self-priming. The plasmid pBR 322 is digested with Pst I endonuclease and homopoly(dG) tails introduced at its 3' ends by terminal transferase. The double-stranded cDNA derived from poly(A) mRNA is likewise tailed with poly(dC). The two tailed DNAs are annealed and the mixture is used to transform the bacterial host E. coli HB101 by the calcium chloride shock procedure.

The resulting transformants may be individually examined, but it is convenient to pool them into groups of 100–150 (a total of 25 groups) for preliminary screening. For each group, DNA is prepared by equilibrium density gradient centrifugation. (See generally, Szybalski et al., "Equilibrium Density Gradient Centrifugation", in Cantoni et al., Eds., Proc. in Nucleic Acid Res., 2, 311 (1971), and references cited therein.) The DNA from each pool is digested with the restriction endonuclease HhaI. The Pst site in pBR 322 into which the cDNAs are inserted is flanked by HhaI sites at a distance from the two ends of the insert of 22 and 315 nucleotides, respectively. This increases the size of cDNA inserts by 337 nucleotides and therefore increases the likelihood that shorter cDNA inserts move higher than the pBR 322 fragment in agarose gels.

The Hha digest of each pool is electrophoresed on 1.5% agarose gel and Southern blots of these gels are hybridized to the 30-nucleotide probe which is labeled at its 5' end with $^{32}$P-labeled phosphate. Only one DNA band from only one pool reveals hybridization with the 30-nucleotide probe. The colonies from that pool are streaked individually and screened as above with the same labeled 30-nucleotide probe. Only one colony shows hybridization. The plasmid DNA from this colony is prepared by the equilibrium density centrifugation procedure.

The recombinant plasmid is digested with Pst I endonuclease and the cDNA insert is purified on 4% acrylamide gels. The size of the cDNA insert is estimated by electrophoresis alongside known size markers to be about 1400 base pairs. The insert includes the nucleic acid sequence coding for the variable region of the antigen which is responsible for its specificity. The cDNA insert is digested with endonuclease Sau 96I which gives a largest fragment of about 700 base pairs in length, along with several small fragments ranging in length from less than 100 base pairs to about 175 base pairs. The 700 nucleotide fragment constitutes the 3' end of the cDNA clone, based on gene mapping data. This fragment is isolated, labeled at its 5' end with polynucleotide kinase and $^{32}$P ATP, and redigested with Hinf I to give two fragments about 500 and 200 base pairs long. The partial nucleotide sequence of the 500 base pair fragment is determined by two different sequencing procedures to be certain of the result; the Maat-Smith procedure (Maat et al, Nucl. Acid. Res., 5, 4537 (1978)) as well as the chemical degradation procedure (Maxam et al, Proc. Natl. Acad. Sci. USA, 74, 560 (1977)).

Table 1 shows the correspondence between the nucleotide sequence from this region of the cDNA clone and the amino acid sequence from position 223 to 269 of the HLA-B7 antigen (Orr et al., Proc. Natl. Acad. Sci. USA, 76, 4395 (1979)). Except for the amino acid at position 242 (glu), the nucleotide sequence corresponds exactly with the amino acid sequence. Position 242 is coded for by CAG, the codon for glutamine (gln), and the glutamate in the reported amino acid sequence is probably an artifact arising from adventitious hydrolysis.

TABLE I

| HLA—B7(NH$_2$) | ... | glu | asp | gln | thr | gln | asp | thr | glu | leu | val |
|---|---|---|---|---|---|---|---|---|---|---|---|
| cDNA 5' | ... G | GAC | CAG | ACT | CAG | GAC | ACT | GAG | CTT | GTG |

| glu | thr | arg | pro | ala | gly | asp | arg | thr | phe | glu | lys | trp | ala |
|---|---|---|---|---|---|---|---|---|---|---|---|---|---|
| GAG | ACC | AGA | CCA | GCA | GGA | GAT | AGA | ACC | TCC | <u>CAG</u> | AAG | TGG | GCA |

| ala | val | val | val | pro | ser | gly | glu | glu | gln | arg | tyr | thr | cys |
|---|---|---|---|---|---|---|---|---|---|---|---|---|---|
| GCT | GTG | GTG | GTG | CCA | TCT | GGA | GAA | GAG | CAG | AGA | TAC | ACA | TGC |

| his | vol | gln | his | glu | gly | leu | pro | lys | pro |
|---|---|---|---|---|---|---|---|---|---|
| CAT | GTA | CAG | CAT | GAG | GGG | CTG | CCG | AAG | CCA |

Because of the high degree of homology between the various HLA genes, the cDNA clone for HLA-B7 antigen will hybridize with all of the other genes for antigens in the HLA-A and HLA-B series and possibly the HLA-C series. Thus, it is possible to isolate and identify a large family of clones for a wide range of histocompatibility antigens. These clones, in turn, can be used to produce labeled HLA antigens by growth with 14C-labeled and/or 35S-labeled methionine in the minicell system. Under these conditions, only plasmid coded proteins would be labeled. Using the long-lasting 14C-isotopes, a set of labeled reagents can be produced that can be used for rapid serotyping of individuals for histocompatibility antigen types. The 14C-labeled antigens could be used with various antisera alone and in the presence of extracts of cells or cell membranes from the individual to be tested. Immunoprecipitati of the radioactive probe would be blocked only if the tested individual had a histocompatibility type sharing antigenic specificity with that particular probe.

Monoclonal antibodies have been produced against various HLA antigens (Brodsky et al, *Immunol. Rev.*, 47, 3 (1979)), but this has in the past been a very complex and difficult task. The use of plasmids producing individual HLA proteins isolated and identified according to the present method greatly simplifies this process, and is capable of generating purified antigens that are fully characterized at the nucleic acid level. These antigens can easily generate highly specific antibodies and can be used to produce specific monoclonal antibodies without the difficulties encountered using earlier techniques.

The general approach for cloning cDNAs from minor mRNA components of an mRNA extract can be applied to isolate and identify a variety of other genes of biological and medical interest. These include any gene coding for a polypeptide for which short amino acid sequences are known. Methods are available to sequence very small amounts of proteins, which means that a DNA segment can be cloned even though both the protein and its corresponding mRNA are present in very low amounts and are extremely difficult to isolate and characterize fully.

Amino acid sequences are already available for certain proteins which have not yet been cloned, and the present method could therefore be easily applied to the production of clones for, e.g., coagulation factors such as fibrinogen, prothrombin and proteins in the earlier stages of blood clotting which are present in lesser abundance, proteins of the complement system, and peptide hormones that have not yet been susceptible to existing cloning procedures. While a variety of procedures have been used to clone many of the genes for peptide hormones from pituitary parathyroid, intestinal mucosa and central sources, genes for other hormones have not been cloned successfully. These include, for example, the parathyroid hormone calcitonin and the various hypothalamic peptides that control pituitary activity, such as thyrotrophin releasing factor, corticotrophin releasing factors, peptides suppressing the excretion of growth hormone, and the like (Snyder, *Science*, 209, 976 (1980)), vitamin B-12 binding protein, enzymes that are deficient in various disorders such as Tay-Sachs disease, or enzymes of glycogen metabolism, antigens associated with tumor cells and various types of lymphocytes.

A further advantage of the present procedure is that one need not even use entirely pure proteins. As long as one protein is the major component in a mixture, the amino acid sequence of a single degradation product of the protein, e.g., a cyanogen bromide or a large tryptic digest fragment, can give sufficient information to design a primer sequence and produce and identify appropriate probes.

It will be understood that the clones produced by the present method can be modified according to techniques well known in the art to optimize the recombinant plasmid for expression of the desired polypeptide. The particular types of optimization will generally be apparent to the skilled art worker.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples; all temperatures are set forth uncorrected in degrees Celsius; unless otherwise indicated, all parts and percentages are by weight.

Chemicals for oligonucleotide synthesis are as disclosed in Itakura et al., *J. Am. chem. Soc.*, 97, 7327 (1975). Sources of materials include: dNTPs, ddNTPs and oligo(dT) cellulose, from Collaborative Research, Waltham, Mass.; reverse transcriptase from avian myeloblastosis virus, from Life Sciences, Inc., St. Petersburg, Fla.; $\gamma$-$^{32}$P-ATP, of specific activity 3000 ci/mM, from New England Nuclear, Boston Mass.; RPMI-1640 media and *E. coli* tRNA, from Gibco, Grand Island, N.Y.; restriction endonucleases, from New England Biolabs, Beverly, Mass. and/or Bethesda Research Labs, Bethesda, Md.; snake venom phosphodiesterase, from Worthington Biochemical Corp., Freehold, N.J.; calf thymus DNA, from Sigma, St. Louis, Mo.; DNase, from Boehringer-Mannheim, Indianapolis, Ind.

Polynucleotide kinase is prepared according to Richardson, *Proc. Natl. Acad. Sci. USA*, 54, 158 (1965).

Human lymphoblastoid cell line RPMI 4265 (HLA-A2; A2, B7, B12) is used as a source of mRNA in these examples. However, any cell line which is homozygous B7 can be used, e.g., GM3161 RI640 201 0300 a specifically characterized human lymphocyte culture, available commercially from the Human Genetic Mutant Cell Repository, Institute for Medical Research, Camden, N.J. Construction of lymphoblastoid cell lines is described, generally by Moore, "Cell Lines From Humans With Hemaopoetic Malignancies", in Fogh, Ed., *Human Tumor Cells In Vitro*, pp 229–332 (Plenum Press, 1975).

EXAMPLE I

Preparation of poly(A) mRNA

RPMI 4265 cells are grown in RPMI 1640 media containing fetal calf serum, glutamate, pyruvate, penicillin and streptomycin to a density of $4 \times 10^5$ cells/ml. RNA is extracted as described by Ghosh et al., *J. Biol. chem.*, 253, 3643 (1978), except that phenol:chloroform: isoamyl alcohol (100:100:1) is used in place of phenol extraction. Enrichment for poly(A) mRNA is achieved by oligo(dT) cellulose column chromatography.

EXAMPLE II

Synthesis and characterization of labeled oligonucleotide primer

The primer 3'TACACCTCTTC5' is chemically synthesized by the triester method. The general conditions for deblocking and coupling reactions are described first, and the specific steps are then outlined. The following abbreviations are used:

DMT: Dimethoxytrityl
Bz: Benzoyl
P: Phosphotriester group (protected) (P-O⁻ indicates deblocked function)
Ar: p-Chlorophenyl
CE: β-Cyanoethyl
TEA: Triethylamine
BSA: Benzenesulfonic acid
TPST: Triisopropylbenzenesulfonyltetrazole
C: Deoxyribosylcytosine
A: Deoxyribosyladenine
T: Deoxyribosylthymine

Deblocking of an oligonucleotide with TEA to remove the CE group

To a solution of fully protected oligonucleotide (0.1 m mole) in anhydrous pyridine (10 ml) is added TEA (2 m moles). The reaction is complete in 2-3 hours as judged by silica gel thin layer chromatography. The solution is then evaporated to a foam in order to remove excess TEA and acrylonitrile liberated during the deblocking reaction. The foamy material is used as such in the coupling reaction.

Deblocking of an oligonucleotide with BSA to remove the DMT group

The solution of an oligonucleotide (0.1 mmole in 10 ml of chloroform: methanol (7:3) is cooled in ice water. Then 100 mg of BSA is added to it, with stirring. The reaction is monitored by silica gel thin layer chromatography. Upon completion, after neutralization with a solution of 5% sodium bicarbonate, the reaction mixture is extracted with chloroform. The solvents are evaporated under vacuum.

Coupling reaction of oligonucleotides with TPST to lengthen the chain

To 0.1 mmole of TEA- deblocked oligonucleotide is added 0.12 mmole of BSA- deblocked oligonucleotide. The mixture is dissolved in 10 ml of dry pyridine, the solution is evaporated to dryness, and the syrupy residue is redissolved in 5 ml of dry pyridine, followed by addition of 0.3 mmole of TPST. After stirring at room temperature for 1 to 5 hours, the reaction mixture is decomposed with distilled water (0.2 ml). The resultant solution is evaporated to a gum in vacuo. The gum is dissolved in ice-cold chloroform (20 ml) followed by neutralization of acid with a 5% solution of sodium bicarbonate in an ice-water bath. The chloroform layer is separated and the aqueous layer is washed twice with chloroform (15 ml each), dried over anhydrous sodium sulfate and evaporated to dryness. The crude mixture is purified by silica gel chromatography.

The reaction sequence is shown schematically as follows:

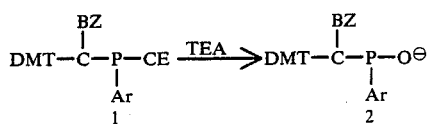

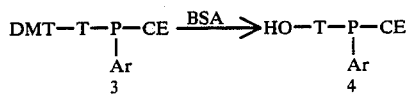

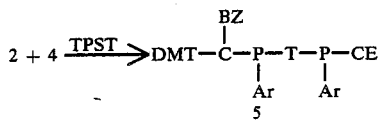

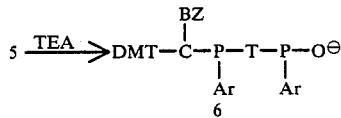

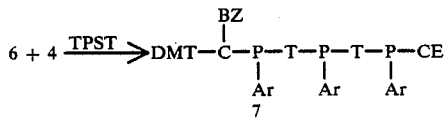

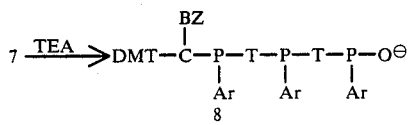

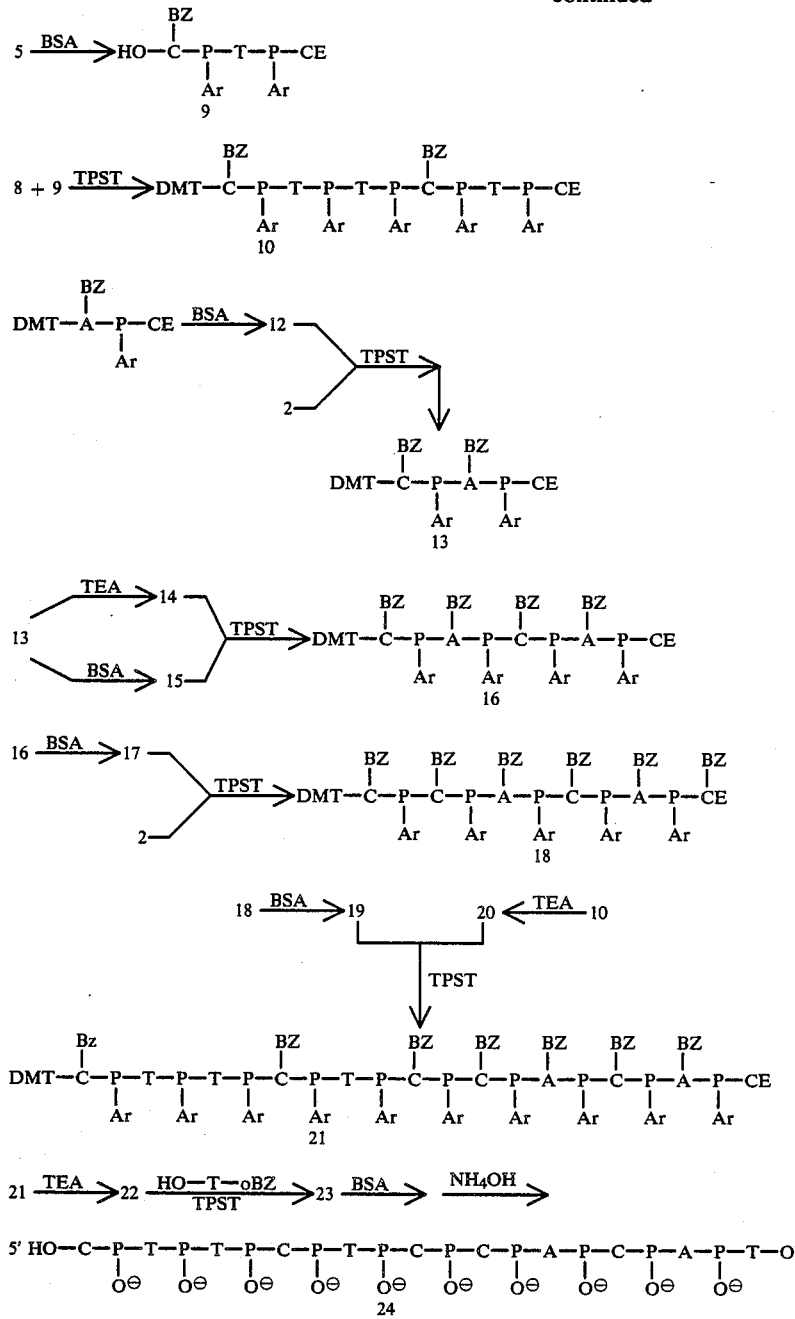

The primer is then phosphorylated at the 5' end with $^{32}$p-ATP and T4 polynucleotide kinase to a specific activity of 1000-1500 ci/mmole. A mixture of 0.5 μg of primer and 240 p mole of $^{32}$p-ATP (3000 Ci/mmole) is incubated in 100 μL of Tris H+pH 8.5 with 10 units of T4 polynucleotide kinase at 37° C. for 40 minutes. The labled primer is purified on 15% polyacrylamide gel, eluted with 0.1 M saline sodium citrate (SSC) (3 ml). The eluent is concentrated and desalted by passage over a column of Sephadex G-10 followed by lyophilization.

The primer is characterized by the two dimensional electrophoresis homochromatography technique of Jay et al., Nucl. Acid Res., 1, 331 (1979). The partial snake venom phosphodiesterase digestion mixture (15 ul) contains 20 mM Tris H+ pH 8.5, 10 mM MgCl$_2$, labeled primer (100,000 cpm), 1 ug of calf thymus DNA, 1 ul of 1 ug/ml DNase, and 3 ul of 0.2 mg/ml snake venom phosphodiesterase at 37° C. Aliquots of 2-3 ul are withdrawn after every three minutes into 3 ul of 100 mM EDTA. The total reaction mixture is then evaporated to dryness, dissolved in 5 ul of water, spotted on a cellulose acetate strip (2×50 cm$^2$) and electrophoresed at 3000 volts for 40 min. After transfer to DEAE cellulose plates, the second dimension is run in 25% homo-B (homo B: 8M urea in 1:3 ratio) until the orange dye is 10 cm from the top. (Homo-B is a mixture of 7M urea and a partial hydrolysate of E. coli tRNA with KOH; Brownlee et al., Eur. J. Biochem., 11, 395 (1969).

EXAMPLE 3

Pre-hybrididization of primer/RNA mixture and probe synthesis

First, 0.25 ug (75 p moles) of $^{32}$P-labeled primer is mixed with 80 ug of the poly(A)-RNA of Example 1 in 60 ul of 80 mM KCl. The mixture is then heated to 90° C. for 10 min, followed by addition of 5 ul of 1M Tris H+pH 8.3. This mixture is incubated for 2 hr at 41° C. The cDNA synthesis is performed using the above primer/RNA mixture. Each of the four dideoxynucleoside triphosphate terminated cDNA synthesis reactions (100 ul) contains the above primer/RNA mixture (60 ul), 5 mM MgCl$_2$,10 mM dithiothreitol (DTT), 500 uM dideoxynucleoside triphosphate, 500 uM each of the other three deoxynucleoside triphosphates and 5 ul of (30 units/ul) reverse transcriptase. In each case, the reaction is incubated at 41° C. for 3 hr; 125 ul of water is added, followed by extraction with 100 ul of phenol: chloroform (1:1). The precipitate is dissolved in 25 ul of 0.1M NaOH and incubated at 41° C. for 1 hr. An equal volume of 8 M urea, 0.05% xylenecyanol/0.05% bromophenol blue is added. The mixture is heated at 90° C. for 1 minute and layered on 12.5% acrylamide-7 M urea gel (40×20 cm). The electrophoresis is performed in 50 mM Tris borate pH 8.3, 1 mM EDTA.

EXAMPLE 4

Characterization of cDNA products obtained from dideoxynucleoside triphosphate terminated cDNA synthesis An individual cDNA band is cut out from the gel, homogenized and soaked overnight with 3.5 ml of 0.1 X SSC. After centrifugation, 20 ug of E. coli tRNA is added to 3 ml of the supernatant. The supernatant is made 0.3M in sodium chloride and precipitated with 3 volumes of ethanol. The precipitate is dissolved in 50 ul of water, centrifuged to remove residual acrylamide and then evaporated to dryness. The partial snake venom phosphodiesterase digestion mixture (15 ul) contains 20 mM Tris H+ pH 8.5, 10 mM MgCl$_2$, labeled cDNA, 1 ug of calf thymus DNA, 1 ul of 1 ug/ml DNase, and 3 ul of 0.2 mg/ml snake venom phosphodiesterase at 37° C. Aliquots of 2-3 ul are withdrawn after every three minutes into 3 ul of 100 mM EDTA. The total reaction mixture is then evaporated to dryness, dissolved in 5 ul of water, spotted on a cellulose acetate strip (2×50 cm$^2$) and electrophoresed at 3000 volts for 45 min to 1 hr. After transfer to DEAE cellulose plates, the second dimension is run in 75% homo-B (Homo B: 8M Urea in 3:1 ratio) until the orange dye is 2 to 5 cm from the top. The homochromotography in 75% homo-B is run for 16 hours at 63° C. in order to achieve better resolution of the longer oligonucleotides of the partial digest.

Sequencing is performed on any bands for 15 or more nucleotides in the ddGTP run and bands for 15, 18, 21, 24, 27 and 30 nucleotides in the ddTTP run. From the nature of the dideoxy G reaction, a G residue is not expected between the 3' end of the primer sequence and the 16th residue of the cDNA product. This is useful in drawing "branches", each representing a two-dimensional map of the individual cDNA product within the 16th position band. In fact, a 30-nucleotide oligomer from the ddTTP run has the sequence 5'CTTCTCCACATCACAGCAGCGAC-CACAGCT3' which corresponds to the mRNA sequence 5'AGCUGUGGUCGCUGCUGUGAUGUG-GAGAAG3', coding for NH2-Ala-Val-Val-Ala-Ala-Val-Met-Trp-Arg-Arg. A 16-nucleotide oligomer from the ddGTP run has the sequence 5'CTTCTCCACAT-CACAG3', the first half of the 30-nucleotide sequence. The 30-nucleotide long probe (20,000 cpm) was used to identify the HLA cDNA clone.

EXAMPLE 5

Construction and screening of cDNA library

The cDNA library is constructed from the cell line RPMI 4265. the poly(A) mRNA of Example 1 is reverse transcribed using oligo(dT) as primer according to the procedure of Buell et al., J. Biol. Chem., 253, 2483(1978). The second strand of the cDNA is synthesized with the proteolytic fragment of DNA polymerase I, followed by digestion with S1 nuclease to remove the hairpin structure resulting from self-priming, according to the procedure of Buell et al., J. Biol. Chem., 253, 2483(1978). The resultant double-stranded cDNA is tailed with poly(dC) at its 3' ends according to the procedure of Nelson et al., Methods Enzymol., 68, 41(1979).

The plasmid pBR322 is di9ested with Pst I endonuclease and tailed with homopoly(dG) at its 3' ends according to the procedure of Nelson et al., ibid. The tailed plasmid DNA and the tailed cDNA are annealed, and the resultant recombinant plasmids are used to transform the E. coli K-12 mutant strain HB101 by the calcium chloride shock procedure of Katcoff et al., Proc. Natl. Acad. Sci. USA, 77, 960(1980).

The resultant transformants are pooled into groups of 100-150 (total 25 groups) and inoculated at a density of approximately 1×10$^7$ bacteria/ml in complex liquid medium (i.e. L. broth) and grown with shaking at 37° C. until reaching a density of 2—6×10$^8$ bacteria/ml. Chloramphenicol is added to a final concentration of 20 ug/ml (this step is optional) and the bacteria are incubated an additional 12-16 hr at 37° C. The bacteria are concentrated by centrifugation and the suspended in 5 ml 0.05M Tris-HCl pH 8.0/25% sucrose (N.B. all values are based on an inoculated starting culture of 50-1000 ml). While on ice, 0.5 ml of a solution of 20 mg lysozyme/ml is added and briefly swirled. Precooled 0.5M EDTA pH 8.0 is added,(0.5 ml) briefly swirled and incubated for 5 min on ice. Lysis is completed by the addition of 3 ml of 3x Triton mix (3 ml 10% Triton X100; 75 ml of 0.25M EDTA; 15 ml 1M Tris pH 8.0; 7 ml H$_2$O) and incubated on ice for 10 min. The later bacteria are centrifuged at 20,000 rpm for 30 min in a SS-34 rotor. The supernatant is decanted and 0.9 g of CsCl and 0.1 ml of ethidium bromide (EtBr)(10 mg EtBr/ml) are added per ml of supernatant. The equilibrium gradient is generated by centrifuging at approximately 200,000 G for 36-48 hr and the plasmid band is withdrawn with a syringe. The EtBr is removed by extracting with isopropanol equilibrated with 0.5M Tris pH 8.0; 0.01M EDTA pH 8.0; 0.05M NaCl that has been saturated with CsCl. The CsCl is removed by dialysis and 5 mM Tris pH 8.0; 1 mM EDTA.

To insure better separation of the cDNA insert, 2 ug of DNA from each pool is incubated in 20 ul of 50 mM NaCl, 6 mM tris H+pH 7.9, 6 mM MgCl$_2$, 5 mM mercaptoethanol and 2 units of HhaI at 37°C. for 1 hr. The digests are electrophoresed on 1.5% agarose gel. the gel is blotted to a nitrocellulose filter as described by Southern, J. Mol. Biol., 98, 503 (1975). The filter is washed with 2×SSC, air dried, and heated at 68°–80° C. for 5 hr under vacuum. The dried filter is presoaked in 3×SSC, 1×Denhardt's (0.02% polyvinyl pyrrolidone, 0.02% Ficoll, 0.02% BSA) at 50° C. for 1 hr. It is then incubated with the $^{32}$P-labeled 30-nucleotide probe (20,000 cpm) of Example 4, in 25ml of 3×SSC, 1×Denhardt's, 0.1% SDS (sodium dodecyl sulfate) at 50° C. for 36 hours followed by washing once with 3×SSC, 1×Denhardt's and twice with 2×SSC at 50° C. After air drying, it is subjected to autoradiography at −70° C. with an intensifying screen.

The colonies from the one pool showing hybridization are streaked and hybridized with the same 30-nucleotide probe (Grunstein et al., *Proc. Natl. Acad. Sci. USA*, 72, 3961 (1975)). Only one colony from that pool hybridizes to the probe. Each pool of DNA before Southern blotting is complex, showing the extremely sensitive separation achieved by the present method.

The isolated plasmid DNA from the recombinant clone, obtained by insertion of cDNA coding for HLA-B7 antigen protein and including a nucleic acid sequence coding for the variable region of HLA-B7, is denoted pDPO01. A deposit of this plasmid, *Escherichia coli pDPO01 DNA*, has been made in the American Type Culture Collection, Rockville, MD., and has been assigned ATCC No. 40032. The clone itself, *Escherichia coli pDPO01*, has also been deposited, and is assigned ATCC No. 31748.

EXAMPLE 6

Nucleotide sequence of the cDNA clone

The plasmid DNA from recombinant clone is digested with restriction endonuclease Pst I. The cDNA insert is approximately 1400 base pairs long, as determined by electrophoresis alongside DNAs of known base pair length.

The insert is isolated by electrophoresis on 4% acrylamide gel. The isolated DNA (20 ug) is incubated in 60 mM NaCl, 6 mM Tris H+ pH 7.4, 15 mM MgCl$_2$, 6 mM mercaptoethanol and 10 units of Sau 96 I at 37° C. for 2 hr followed by electrophoresis on 4% acrylamide gel. The largest fragment, about 700 base pairs long, is isolated, labeled at its 5′ end with polynucleotide kinase and $^{32}$P-ATP, and redigested with HinfI. the mixture is electrophorcsed on 5% acrylamide gel. Two fragments of approximately 500 base pairs long and 200 base pairs long labeled at one end are isolated.

The partial nucleotide sequence of the 500 base pair fragment starting from its 5′ end, determined by the procedure of Maat et al., *Nucl. Acid Res.*, 5, 4537 (1978), as well as a second partial sequencing, effected by the chemical degration procedure of Maxam et al., *Proc. Natl. Acad. Sci. USA*, 74, 560 (1977)), gives the partial sequence of Table I.

The preceding examples can be repeated with similar success by substituting other polypeptides for which a partial amino acid sequence is known or can readily be determined, and by using other cloning vehicles, hosts, chain-termination procedures, sequencing procedures, restriction endonucleases, oligonucleotide primers, cell lines and/or other generically or specifically described materials and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a recombinant cloning vehicle comprising an inserted human gene,
    the improvement wherein said cloning vehicle is isolated from a recombinant clone which is isolated and identified by a process comprising the steps of:
    (a) effecting cDNA synthesis on a mixture of mRNAs containing a target mRNA coding for a major histocompatibility antigen, and isolating the resultant cDNA mixture;
    (b) inserting said resultant cDNA into recombinant cloning vehicles, and transforming hosts with said vehicles; and
    (c) separating the transformants and isolating and identifying a recombinant clone containing a DNA segment which is homologous over at least a portion thereof to at least one oligonucleotide probe specifio for said DNA segment, said identification being effected by hybridization with said probe; wherein said probe is an extension of the nucleotide sequence of an oligonucleotide primer having a nucleotide sequence complementary to a region of said target mRNA coding for a portion of said amino acid sequence, said oligonucleotide probe being produced by separately effecting cDNA synthesis in the presence of said oligonucleotide primer and only three deoxynucleotide triphosphates, isolating and separating extended cDNA fractions having at least three more nucleotides than said primer, sequencing said extended fractions, and recovering at least one oligonucleotide complementary to a longer region of said target mRNA coding for a longer portion of said known amino acid sequence.

2. The cloning vehicle of claim 1, wherein said antigen is coded for on the HLA-B locus.

3. The cloning vehicle of claim 1, which is a plasmid.

4. The cloning vehicle of claim 2, which is the recombinant plasmid obtained by inserting said DNA segment, containing the partial nucleotide sequence (5′) dG GAC CAG ACT CAG GAC ACT GAG CTT GTG GAG ACC AGA CCA GCA GGA GAT AGA ACC TTC CAG AAG TGG GCA GCT GTG GTG GTG CCA TCT GGA GAA GAG CAG AGA TAC ACA TGC CAT GTA CAG CAT GAG GGG CTG CCG AAG CCA, into the plasmid pBR 322.

5. In a recombinant host cell derived from a host transformed with a recombinant cloning vehicle comprising an inserted DNA segment coding for at least one desired heterologous polypeptide, at least a short amino acid sequence of which is known,
    the improvement wherein said cloning vehicle is one of claim 1.

6. The recombinant host cell of claim 5, wherein said antigen is coded for on the HLA-B locus.

7. The recombinant host cell of claim 6, which is the *E. coli* strain HB101 transformed by a recombinant plasmid derived from the plasmid pBR 322 and containing an inserted DNA segment coding for a human major histocompatibility antigen coded for on the HLA-B locus, said segment being inserted at the Pst I cleavage site of pBR 322; wherein said inserted DNA segment contains the partial nucleotide sequence (5′) dG GAC CAG ACT CAG GAC ACT GAG CTT GTG GAG ACC AGA CCA GCA GGA GAT AGA ACC TTC CAG AAG TGG GCA GCT GTG GTG GTG CCA TCT GGA GAA GAG CAG AGA TAC
ACA TGC CAT GTA CAG CAT GAG GGG CTG
CCG AAG CCA.

8. The recombinant host cell of claim 5, wherein said process further comprises repeating step (c) at least once, using the oligonucleotide probe from the preceding iteration as a new primer, and recovering an extended oligonucleotide probe complementary to a longer region of said target mRNA coding for a longer portion of said known amino acid sequence.

9. The cloning vehicle of claim 1, wherein said process further comprises repeating step (c) at least once, using the oligonucleotide probe from the preceding iteration as a new primer, and recovering an extended oligonucleotide probe complementary to a longer region of said target mRNA coding for a longer portion of said known amino acid sequence.

10. The cloning vehicle of claim 1, wherein in step (c) of said process, said primer has from 10 to 14 nucleotides.

11. The cloning vehicle of claim 1, wherein in step (c) of said process, said separately effected cDNA synthesis is effected in the further presence of one dideoxynucleoside triphosphate having a different base from said three deoxynucleoside triphosphates; and wherein said extended cDNA fractions have at least four nucleotides more than said primer.

12. The cloning vehicle of claim 11, wherein said primer has from 10 to 14 nucleotides.

13. A molecular cloning vehicle comprising a recombinant cloning vehicle and further comprising an inserted DNA sequence encoding a human major histocompatibility antigen and said inserted DNA sequence hybridizing to the cDNA insert of a recombinant clone said recombinant clone being isolated and identified by a process comprising the steps of:
(a) effecting cDNA synthesis on a mixture of mRNAs containing a target mRNA coding for a major histocompatibility antigen, and isolating the resultant cDNA mixture;
(b) inserting said resultant cDNA into recombinant cloning vehicles, and transforming hosts with said vehicles; and
(c) separating the transformants and isolating and identifying a recombinant clone containing a DNA segment which is homologous over at least a portion thereof to at least one oligonucleotide probe specific for said DNA segment, said identification being effected by hybridization with said probe; wherein said probe is an extension of the nucleotide sequence of an oligonucleotide primer having a nucleotide sequence complementary to a region of said target mNRA coding for a portion of said amino acid sequence, said oligonucleotide probe being produced by separately effecting cDNA synthesis in the presence of said oligonucleotide primer and only three deoxynuycleotide triphosphates, isolating and separating extended cDNA fractions having at lest three more nucleotides than said primer, sequencing said extended fractions, and recovering at least one oligonucleotide complementary to a longer region of said target mRNA coding for a longer portion of said known amino acid sequence.

14. The cloning vehicle of claim 13, wherein said antigen is coded for on the HLA-B locus.

15. The cloning vehicle of claim 14, which is the recombinant plasmid obtained by inserting said DNA segment, containing the partial nucleotide sequence (5′)dG GAC CAG ACT CAG GAC ACT GAG CTT GTG GAG ACC AGA CCA GCA GGA GAT AGA ACC TTC CAG AAG TGG GCA GCT GTG GTG GTG CCA TCT GGA GA.A GAG CAG AGA TAC ACA TGC CAT GTA CAG CAT GAG GGG CTG CCG AAG CCA, into the plasmid pBR 322.

16. A recombinant plasmid derived from the plasmid pBR 322 and containing an inserted DNA segment coding for a human major histocompatibility antigen coded for on the HLA-B locs, said segment being inserted at the Pst I cleavage site of pBR 322; wherein said inserted DNA sgement contains the partial nucleotide sequence (5′)dG GAC CAG ACT CAG GAC ACT GAG CTT GTG GAG ACC AGA CCA GCA GGA GAT AGA ACC TTC CAG AAG TGG GCA GCT GTG GTG GTG CCA TCT GGA GAA GAG CAG AGA TAC ACA TGC CAT GTA CAG CAT GAG GGG CTG CCG AAG CCA.

17. A recombinant plasmid of *Escherichia coli* pDPO0l, as deposited with The American Type Culture Collection, Rockville, Md., and having ATCC accession No. 40032.

18. A recombinant clone *Escherichia coli* pDPO0l, as deposited with The American Type Culture Collection, Rockville, Md., and having ATCC accession No. 31748.

* * * * *